(12) United States Patent
Fukunishi et al.

(10) Patent No.: US 8,592,582 B2
(45) Date of Patent: Nov. 26, 2013

(54) METHOD FOR PRODUCING PYRIMIDINYLPYRAZOLE COMPOUNDS

(75) Inventors: Hirotada Fukunishi, Yokohama (JP); Naoto Hanyu, Yokohama (JP); Masaru Suetsugu, Yokohama (JP); Takuya Hiruma, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/520,203

(22) PCT Filed: Jan. 5, 2011

(86) PCT No.: PCT/JP2011/050045
§ 371 (c)(1),
(2), (4) Date: Jul. 10, 2012

(87) PCT Pub. No.: WO2011/086955
PCT Pub. Date: Jul. 21, 2011

(65) Prior Publication Data
US 2012/0283441 A1    Nov. 8, 2012

(30) Foreign Application Priority Data

Jan. 18, 2010 (JP) ................................. 2010-007981

(51) Int. Cl.
C07D 403/04 (2006.01)

(52) U.S. Cl.
USPC ........................................ 544/310; 544/331

(58) Field of Classification Search
USPC ................................. 544/310, 331
See application file for complete search history.

(56) References Cited

U.S. PATENT DOCUMENTS

| | | | |
|---|---|---|---|
| 3,865,825 | A | 2/1975 | Hirayama et al. |
| 5,453,514 | A | 9/1995 | Niigata et al. |
| 2009/0036475 | A1 | 2/2009 | Eriksen et al. |
| 2012/0134944 | A1 | 5/2012 | Hanyu et al. |

FOREIGN PATENT DOCUMENTS

| | | |
|---|---|---|
| JP | 42-19593 | 10/1967 |
| JP | 1973-026773 | 3/1973 |
| JP | 48-026773 A | 4/1973 |
| JP | 54-117029 | 9/1979 |
| JP | 54-147921 | 11/1979 |
| JP | 62-000404 | 1/1987 |
| JP | 2003-313450 | 11/2003 |
| JP | 2008-534472 | 8/2008 |
| JP | 2008-534472 A | 8/2008 |
| WO | 2006/100212 A1 | 9/2006 |
| WO | 2009/099192 | 8/2009 |
| WO | 2009/099194 A1 | 8/2009 |

OTHER PUBLICATIONS

English Abstract from Espacenet of JP 62-000404, two pages.
English Abstract from Espacenet of JP 2003-313450, two pages.
English Abstract from Espacenet of JP 2008-534472, two pages.
Konishi, et al., "Fungicidal Activity of Pyrazolylpyrinnidines", Pesticide Science Society of Japan, J. Pesticide Sci, 15, 13-22 (1990), ten pages.
Patent Abstracts of Japan, Publication No. 54-117029, one page.
Patent Abstracts of Japan, Publication No. 54-147921, one page.
Partial English Translation of JP 42-19593, two pages.
Ranjeet Bairwa, et al. "Novel Regiospecific Method for Synthesis of 2-(3,5-Diaryl-4,5-dihydro-1H-pyrazol-1-yl)-4,6-diarylpyrimidines", 'Synthetic Communications', 2008, vol. 38, pp. 943-952, eleven pages.
Helio Gauze Bonacorso, et al. "Regiospecific Cyclization of β-Methoxyvinyl Trifluoromethyl Ketones with Aminoguanidine: A Convenient Method to Obtain Trifluoromethylated 2-[1H-Pyrazol-1-yl] pyrimdines", 'Synthesis', 2001, No. 10, pp. 1505-1508, five pages.
M.I. Al-Ashmawy, et al., "Utility of 2 hydrazino-4,6-dirnethylpyridine in heterocyclic synthesis", Bollettino Chimico Farmaceutico, 1998, 137,4, pp. 110-114, five pages.
International Preliminary Report on Patentability, International Application No. PCT/JP2011/050045, 10 pages.
European Search Report, Application No. 11732825, dated Jul. 18, 2013, 6 pages.

*Primary Examiner* — James O Wilson
*Assistant Examiner* — Ebenezer O Sackey
(74) *Attorney, Agent, or Firm* — Rankin, Hill & Clark LLP

(57) ABSTRACT

The present invention provides a method for producing a pyrimidinylpyrazole compound (1), wherein aminoguanidine (2) or its salt is reacted with a β-diketone compound (3) to produce the pyrimidinylpyrazole compound:

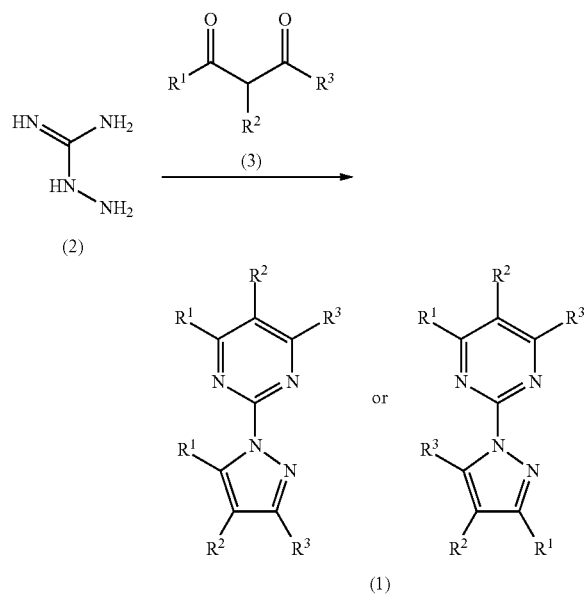

wherein $R^1$ and $R^3$ are each independently an alkyl group having 1 to 4 carbon atoms, and $R^2$ is a hydrogen atom or an alkyl group having 1 to 4 carbon atoms. The method is excellent in the environmental compatibility and economic efficiency.

2 Claims, No Drawings

METHOD FOR PRODUCING PYRIMIDINYLPYRAZOLE COMPOUNDS

RELATED APPLICATIONS

This application claims the priority of Japanese Patent Application No. 2010-7981 filed on Jan. 18, 2010, which is incorporated herein by reference.

FIELD OF THE INVENTION

The present invention relates to a method for producing a pyrimidinylpyrazole compound, and in particular, relates to a method for producing a pyrimidinylpyrazole compound in absence of a solvent or in an aqueous solvent, in one step.

BACKGROUND ART

In the past, among the compounds having a pyrimidinylpyrazole skeleton, compounds having various physiological activities have been known. For example, pyrimidinylpyrazole compounds having potassium channel modulating activity (Patent Literature 1); the control activity of rice blast, helminthosporium leaf spot of rice plant, powdery mildew of cucumber, etc. (Patent Literatures 2 to 4); and analgesic activity (Patent Literature 5) have been reported, respectively. In recent years, a pyrimidinylpyrazole compound having excellent melanin production inhibiting activity and being useful as a whitening agent has been reported (Patent Literature 6).

Various methods have been known for the formation of a pyrimidinylpyrazole skeleton. In Patent Literature 6, for example, the method wherein a pyrimidinylpyrazole compound is produced by the cyclization reaction of a hydrazinylpyrimidine compound with a β-diketone compound is described.

However, this method is poor in economic efficiency because the hydrazinylpyrimidine compound necessary to obtain the intended pyrimidinylpyrazole compound is not commercially available or, even when it is commercially available, it is very expensive. For the synthesis of a necessary hydrazinylpyrimidine compound, one or two steps are needed and an organic solvent may have to be used as the reaction solvent.

In Non-patent Literature 1, the method wherein a β-methoxyvinyl trifluoromethyl ketone compound is reacted with aminoguanidine bicarbonate in ethanol to form a pyrimidinylpyrazoline skeleton, and it is converted to a pyrimidinylpyrazole skeleton by the subsequent dehydration reaction in dichloromethane is described.

In this method, however, an organic solvent is used as the reaction solvent, and the reaction consists of two steps. In addition, for the synthesis of the raw material, β-methoxyvinyl trifluoromethyl ketone compound, an additional step is necessary.

In Non-patent Literature 2, the method wherein a pyrazole ring is directly introduced by the substitution, in ethanol, of the leaving group of a pyrimidine compound to produce a pyrimidinylpyrazole compound is described.

In this method, a pyrimidinylpyrazole compound can be obtained in one step from two raw materials. However, there are problems in that an organic solvent is used as the reaction solvent, and that the raw materials are very expensive and, if they are synthesized, additional steps are necessary.

Accordingly, from the standpoint of environmental compatibility and economic efficiency, a method wherein a pyrimidinylpyrazole compound can be produced from a small number of raw materials and in a small number of steps, as much as possible, and without the use of an organic solvent, which has a high environmental burden, has been awaited.

PRIOR ART LITERATURES

Patent Literatures

Patent Literature 1: WO2006/100212
Patent Literature 2: Japanese Unexamined Patent Publication No. S54-117029
Patent Literature 3: Japanese Unexamined Patent Publication No. S54-147921
Patent Literature 4: Japanese Unexamined Patent Publication No. S62-404
Patent Literature 5: Japanese Examined Patent Publication No. S42-19593
Patent Literature 6: WO2009/099192

Non-Patent Literatures

Non-patent Literature 1: Synthesis, 2001, (10), 1505-1508.
Non-patent Literature 2: Bollettino Chimico Farmaceutico, 1998, 137, 4, 110-114.

SUMMARY OF THE INVENTION

Problem to be Solved by the Invention

The present invention was made in view of the above-described background art, and the object is to provide a production method, excellent in the environmental compatibility and economic efficiency, of a pyrimidinylpyrazole compound.

Means to Solve the Problem

The present inventors have diligently studied; as a result, the present inventors have found that a pyrimidinylpyrazole compound can be obtained in one step by reacting aminoguanidine or its salt and a β-diketone compound and that this reaction successfully proceeds even in the absence of a solvent or in an aqueous solvent such as water, thus completing the present invention.

That is, the production method of the present invention is a method for producing a pyrimidinylpyrazole compound represented by general formula (1), wherein aminoguanidine represented by general formula (2) or its salt is reacted with a β-diketone compound represented by general formula (3) to produce the pyrimidinylpyrazole compound:

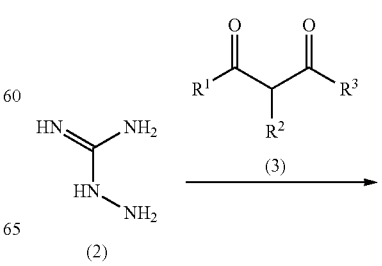

-continued

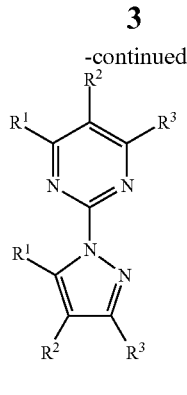

(1)

wherein $R^1$ and $R^3$ are each independently an alkyl group having 1 to 4 carbon atoms, and $R^2$ is a hydrogen atom or an alkyl group having 1 to 4 carbon atoms.

Also, the present invention provides the method for producing the pyrimidinylpyrazole compound, wherein the reaction is carried out in the absence of a solvent.

Also, the present invention provides the method for producing the pyrimidinylpyrazole compound, wherein the reaction is carried out in an aqueous solvent.

Also, the present invention provides the method for producing the pyrimidinylpyrazole compound, wherein the reaction is carried out in water.

Also, the present invention provides the method for producing the pyrimidinylpyrazole compound, wherein a 2-fold or higher molar equivalent of the β-diketone compound is used with respect to aminoguanidine.

Also, the present invention provides the method for producing the pyrimidinylpyrazole compound, wherein the reaction is carried out in the presence of a base.

Also, the present invention provides the method for producing the pyrimidinylpyrazole compound, wherein the base is selected from the group consisting of hydroxides, carbonates and acetates of alkali metals or alkaline earth metals.

Effect of the Invention

According to the method of the present invention, a pyrimidinylpyrazole compound can be produced in one step from a commercially easily available and relatively low-molecular raw material. In addition, the reaction can be carried out in the absence of a solvent or in an aqueous solvent; thus the environmental burden is low and the economic efficiency is excellent.

MODE FOR CARRYING OUT THE INVENTION

In the production method of the present invention, as shown in the below reaction formula, a pyrimidinylpyrazole compound (1) can be obtained in one step by the reaction of aminoguanidine (2) or its salt and a β-diketone compound (3) in the absence of a solvent or in a solvent.

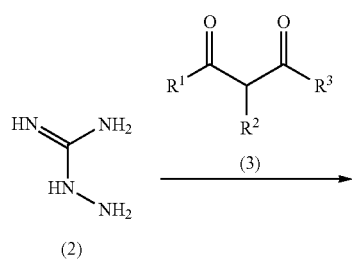

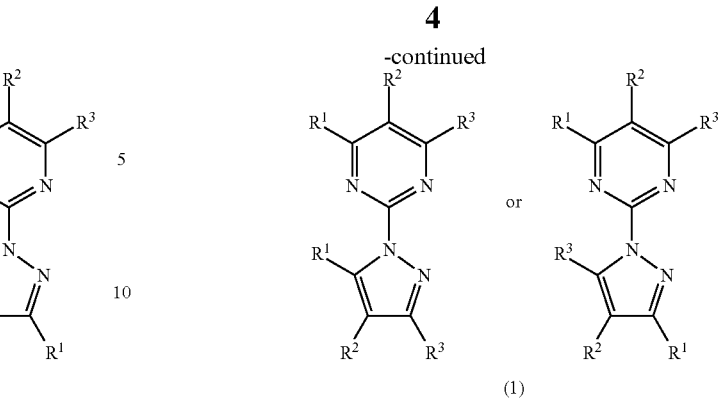

(1)

In the above reaction formula, $R^1$ and $R^3$ are each independently an alkyl group having 1 to 4 carbon atoms, and $R^1$ and $R^3$ are preferably identical.

$R^2$ is a hydrogen atom or an alkyl group having 1 to 4 carbon atoms.

In the present invention, an alkyl group having 1 to 4 carbon atoms can be linear, branched, or cyclic. Examples thereof include methyl, ethyl, n-propyl, isopropyl, n-butyl, sec-butyl, isobutyl, tert-butyl, cyclopropyl, and cyclobutyl.

As an example of the pyrimidinylpyrazole compound, a compound wherein $R^1$ and $R^3$ are each a linear or branched alkyl group having 1 to 4 carbon atoms can be listed.

As another example of the pyrimidinylpyrazole compound, a compound wherein at least one of $R^1$ and $R^3$ is methyl can be listed.

As another example of the pyrimidinylpyrazole compound, a compound wherein $R^2$ is a hydrogen atom, methyl, or ethyl can be listed.

As aminoguanidine (2), a salt of aminoguanidine can be used so far as there are no special problems. Examples of the salts include salts with inorganic acids such as hydrochloric acid, carbonic acid, bicarbonic acid, hydrobromic acid, sulfuric acid, and phosphoric acid; and salts with organic acids such as acetic acid, propionic acid, citric acid, lactic acid, oxalic acid, maleic acid, numeric acid, succinic acid, tartaric acid, and methanesulfonic acid. The hydrochloride, bicarbonate, etc. are easily available as commercial products. Aminoguanidine or its salts may also be synthesized by a publicly known method.

In the β-diketone compound (3), $R^1$ to $R^3$ are determined depending upon the intended pyrimidinylpyrazole compound. Examples of the β-diketone compound include acetylacetone, 2,4-hexanedione, 3-methyl-2,4-pentanedione, 2-methyl-3,5-hexanedione, 2,4-heptanedione, 3,5-heptanedione, 3-ethyl-2,4-pentanedione, 2-methyl-3,5-heptanedione, 3,5-octanedione, 2,2-dimethyl-3,5-hexanedione, 3-acetyl-4-methyl-2-pentanone, 3-acetyl-2-hexanone, 2,4-octanedione, 6-methyl-2,4-heptanedione, 3-acetyl-5-methyl-2-hexanone, 3-n-butyl-2,4-pentanedione, 2,4-nonanedione, 2-methyl-3,5-octanedione, 2,2-dimethyl-3,5-heptanedione, 2-methyl-4,6-octanedione, 3,5-nonanedione, 3-tert-butyl-2,4-pentanedione, 4,6-nonanedione, 2,6-dimethyl-3,5-heptanedione, 1-cyclopropyl-1,3-butanedione, 1-cyclopropylpentane-1,3-dione, 1-cyclopropyl-4,4-dimethylpentane-1,3-dione, and 1-cyclobutyl-1,3-butanedione; however, they are not limited by these examples. The β-diketone compounds may be synthesized by a publicly known method or commercial products may be used.

As for the β-diketone compound (3), 2-fold or higher molar equivalent thereof is used with respect to aminoguanidine or its salt. Although there is no upper limit in particular, it is preferable to be less than 5-fold molar equivalent from the standpoint of production cost. If the amount of a β-diketone compound is too small, the reaction will not be satisfactory.

The present reaction can be carried out in the presence of a solvent or in the absence of a solvent. Examples of reaction solvents include hydrocarbon solvents such as toluene, xylene, benzene, hexane, and cyclohexane; alcoholic solvents such as methanol, ethanol, and isopropyl alcohol; tetrahydrofuran; dimethylformamide; dimethyl sulfoxide; water; and their mixed solvents; however, there are no particular limitations so far as the reaction is not adversely affected. When a solvent is used, however, it is preferable to use aqueous solvents such as water or alcoholic solvents, which have a lower environmental burden, from the standpoint of environmental compatibility, and water is especially preferable.

In the recent synthesis reactions, the reaction in the absence of a solvent or the reaction in water, whose environmental burden is low, has been strongly desired from the viewpoint of environmental compatibility. The method of the present invention can satisfy such a requirement.

The reaction can be carried out in the temperature range of 0° C. to 200° C. and preferably in the range of room temperature to 120° C. The reaction can be carried out under pressure; however, it is normally carried out under atmospheric pressure.

The present reaction can be carried out, as necessary, in the presence of a base. One or more bases can be combined. Examples of bases used in the reaction include alkali metal hydroxides such as sodium hydroxide, potassium hydroxide, and lithium hydroxide; alkaline earth metal hydroxides such as barium hydroxide, calcium hydroxide, and magnesium hydroxide; metal alkoxides such as sodium methoxide, sodium ethoxide, and potassium t-butoxide; tetraalkylammonium hydroxides such as tetrabutylammonium hydroxide and benzyltrimethylammonium hydroxide; metal carbonates such as potassium carbonate, sodium carbonate, calcium carbonate, sodium hydrogencarbonate, and potassium hydrogencarbonate; metal hydrides such as sodium hydride, potassium hydride, and calcium hydride; metal acetates such as sodium acetate and potassium acetate; other metal salts of organic acids; alkali metals such as sodium, potassium, and lithium; amines such as triethylamine, diethylamine, 1,8-diazabicyclo(5.4.0)undecene, and 1,5-diazabicyclo(4.3.0)nonene; and mixtures thereof. Among them, the hydroxides, carbonates, and acetates of alkali metals or alkaline earth metals are preferable, and sodium acetate is especially preferable.

When a base is used, the amount of the base can be, for example, 0 to 5-fold molar equivalent with respect to the amount of aminoguanidine or its salt. It is normally 0.2-fold or higher molar equivalent, preferably 0.5 to 2-fold molar equivalent, and more preferably 0.8 to 1.2-fold molar equivalent. The reaction can proceeds without the use of a base; however, a high reaction temperature may be necessary in that case.

EXAMPLES

Hereinafter, the present invention will be explained with reference to representative examples. However, the present invention is not limited by these examples, and the desired pyrimidinylpyrazole compound (I) can be produced with the use of suitable raw materials.

Example 1

To aminoguanidine hydrochloride (manufactured by Tokyo Chemical Industry, purity: 98% or higher) (1.11 g, 10 mmol), acetylacetone (manufactured by Tokyo Chemical Industry, purity: 99% or higher) (2.00 g, 20 mmol) and 2N sodium hydroxide aqueous solution (5 ml) were added, and then stirred at 80° C. for 5 hours. To the reaction mixture, 1N sodium hydroxide aqueous solution was added to adjust the pH to near 13, and the extraction was carried out with ethyl acetate. The extract was dried with anhydrous sodium sulfate, and then dried under reduced pressure to obtain 2-(3,5-dimethylpyrazolo)-4,6-dimethylpyrimidine (1.16 g, 58%).

2-(3,5-Dimethylpyrazolo)-4,6-dimethylpyrimidine (Compound 1-a):

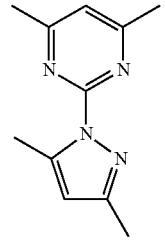

(1-a)

$^1$H-NMR (DMSO-d$_6$) δ: 2.19 (3H, s), 2.45 (6H, s), 2.53 (3H, s), 6.09 (1H, s), 7.17 (1H, s).
$^{13}$C-NMR (DMSO-d$_6$) δ: 13.20, 14.09, 23.26, 108.96, 117.14, 141.44, 148.84, 156.36, 168.03.

Example 2

To aminoguanidine bicarbonate (manufactured by Tokyo Chemical Industry, purity: 99% or higher) (1.36 g, 10 mmol), acetylacetone (2.00 g, 20 mmol) and water (5 ml) were added, and then stirred at 80° C. for 5 hours. To the reaction mixture, 1N sodium hydroxide aqueous solution was added to adjust the pH to near 9, and the extraction was carried out with ethyl acetate. The extract was dried with anhydrous sodium sulfate, and then dried under reduced pressure to obtain 2-(3,5-dimethylpyrazolo)-4,6-dimethylpyrimidine (1.14 g, 56%).

Example 3

To aminoguanidine hydrochloride (5.53 g, 50 mmol), acetylacetone (11.0 g, 110 mmol) was added, and then stirred at 120° C. for 10 hours in the absence of a solvent. To the reaction mixture, 10% sodium hydroxide aqueous solution was added to adjust the pH to near 10, and then the mixture was stirred at 0° C. for 1 hour. The precipitated crystals were collected by filtration, washed with water, and dried under reduced pressure to obtain 2-(3,5-dimethylpyrazolo)-4,6-dimethylpyrimidine (5.00 g, 50%).

Example 4

To aminoguanidine hydrochloride (5.53 g, 50 mmol), acetylacetone (11.0 g, 110 mmol), water (20 ml), and sodium hydroxide (2.00 g, 50 mmol) were added, and then stirred at 80° C. for 5 hours. To the reaction mixture, water (10 ml) and 1N sodium hydroxide aqueous solution (1 ml) were added, and then stirred at 0° C. for 1 hour. The precipitated crystals were collected by filtration, washed with water, and dried under reduced pressure to obtain 2-(3,5-dimethylpyrazolo)-4,6-dimethylpyrimidine (4.41 g, 44%).

Example 5

To aminoguanidine bicarbonate (6.80 g, 50 mmol), water (20 ml) and acetylacetone (11.0 g, 110 mmol) were added, and then stirred at 80° C. for 5 hours. To the reaction mixture, water (10 ml) and 1N sodium hydroxide aqueous solution (1 ml) were added, and then stirred at 0° C. for 1 hour. The precipitated crystals were collected by filtration, washed with water, and dried under reduced pressure to obtain 2-(3,5-dimethylpyrazolo)-4,6-dimethylpyrimidine (4.58 g, 45%).

Example 6

To aminoguanidine bicarbonate (13.96 g, 0.103 mol), water (20 ml) and acetylacetone (22.59 g, 0.226 mol) were added, and then stirred at 80° C. for 9 hours. To the reaction mixture, water (60 ml) was added, and then stirred at room temperature for 1 hour. The precipitated crystals were collected by filtration, washed with water, and dried under reduced pressure to obtain 2-(3,5-dimethylpyrazolo)-4,6-dimethylpyrimidine (11.69 g, 56%).

Example 7

To aminoguanidine hydrochloride (11.47 g, 0.104 mol), water (20 ml), sodium hydroxide (4.15 g, 0.104 mol), and acetylacetone (22.91 g, 0.229 mol) were added, and then stirred at 80° C. for 9 hours. To the reaction mixture, water (60 ml) was added, and then stirred at room temperature for 1 hour. The precipitated crystals were collected by filtration, washed with water, and dried under reduced pressure to obtain 2-(3,5-dimethylpyrazolo)-4,6-dimethylpyrimidine (10.68 g, 51%).

Example 8

To aminoguanidine hydrochloride (1.76 g, 15.9 mmol), water (5 ml), sodium hydroxide (636 mg, 15.9 mmol), and 3-ethyl-2,4-pentanedione (manufactured by Tokyo Chemical Industry, purity: 90.0% or higher) (4.50 g, 35.0 mmol) were added, and then stirred at 80° C. for 8 hours. To the reaction mixture, water (30 ml) was added, and then stirred at 0° C. for 1 hour. The precipitated crystals were collected by filtration, washed with water, and dried under reduced pressure to obtain 5-ethyl-2-(4-ethyl-3,5-dimethylpyrazol-1-yl)-4,6-dimethylpyrimidine (1.35 g, 33%).

5-Ethyl-2-(4-ethyl-3,5-dimethylpyrazol-1-yl)-4,6-dimethylpyrimidine (Compound 1-b): (1-b)

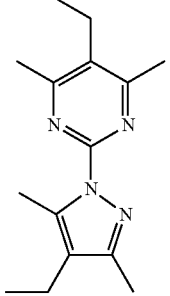

$^{1}$H-NMR (DMSO-$d_6$) δ: 1.05 (3H, t, J=7.7 Hz), 1.12 (3H, t, J=7.7 Hz), 2.18 (3H, s), 2.38 (2H, q, J=7.7 Hz), 2.45 (3H, s), 2.49 (6H, s), 2.66 (2H, q, J=7.7 Hz).
$^{13}$C-NMR (DMSO-$d_6$) δ: 11.50, 11.82, 12.42, 14.68, 15.80, 20.22, 21.12, 120.54, 129.32, 136.64, 147.53, 154.01, 165.39.

Example 9

To aminoguanidine hydrochloride (1.59 g, 14.4 mmol), water (5 ml), sodium hydroxide (576 mg, 14.4 mmol), and 6-methyl-2,4-heptanedione (manufactured by Tokyo Chemical Industry, purity: 97.0% or higher) (4.50 g, 31.6 mmol) were added, and then stirred at 80° C. for 8 hours. To the reaction mixture, water (30 ml) was added, and the extraction was carried out with ethyl acetate (10 ml). The extract was washed with saturated brine, dried with anhydrous sodium sulfate, and then concentrated. The obtained residue (3.83 g) was subjected to silica gel column chromatography (80 g of silica gel, chloroform to chloroform:methanol=100:1) to obtain 4-isobutyl-2-(3-isobutyl-5-methylpyrazol-1-yl)-6-methylpyrimidine (181 mg, 4%) and 4-isobutyl-2-(5-isobutyl-3-methylpyrazol-1-yl)-6-methylpyrimidine (2.05 g, 50%).

4-Isobutyl-2-(3-isobutyl-5-methylpyrazol-1-yl)-6-methylpyrimidine (Compound 1-$c_1$): (1-$c_1$)

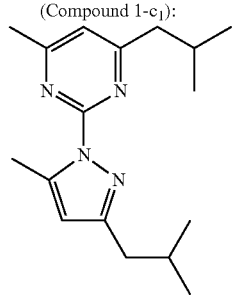

$^{1}$H-NMR (DMSO-$d_6$) δ: 0.93 (6H, d, J=6.8 Hz), 0.93 (6H, d, J=6.8 Hz), 1.88-1.98 (1H, m), 2.12-2.22 (1H, m), 2.45 (2H, d, J=6.8 Hz), 2.49 (3H, s), 2.56 (3H, s), 2.60 (2H, d, J=6.8 Hz), 6.12 (1H, s), 7.16 (1H, s).
$^{13}$C-NMR (DMSO-$d_6$) δ: 14.19, 21.98, 22.21, 23.34, 27.48, 27.89, 36.85, 45.66, 108.41, 117.27, 141.20, 152.54, 156.53, 168.26, 170.49.

4-Isobutyl-2-(5-isobutyl-3-methylpyrazol-1-yl)-6-methylpyrimidine (Compound 1-$c_2$): (1-$c_2$)

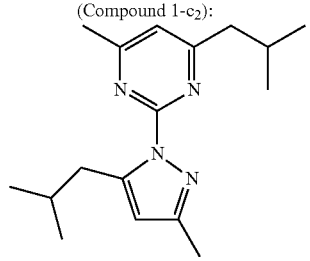

$^{1}$H-NMR (DMSO-$d_6$) δ: 0.86 (6H, d, J=6.8 Hz), 0.93 (6H, d, J=6.8 Hz), 1.83 (1H, septet, J=6.8 Hz), 2.14 (1H, septet, J=6.8 Hz), 2.22 (3H, s), 2.49 (3H, s), 2.60 (2H, d, J=6.8 Hz), 2.90 (2H, d, J=6.8 Hz), 6.10 (1H, s), 7.17 (1H, s).
$^{13}$C-NMR (DMSO-$d_6$) δ: 13.19, 21.89, 21.99, 23.31, 27.44, 27.65, 35.83, 45.68, 108.90, 117.42, 144.76, 148.64, 156.55, 168.28, 170.57.

Example 10

To aminoguanidine hydrochloride (5.52 g, 50 mmol), water (20 ml), acetylacetone (11 g, 110 mmol), and sodium acetate (4.10 g, 50 mmol) were added, and then stirred at 80° C. for 7 hours. To the reaction mixture, water (20 ml) was added, and then stirred at room temperature overnight. The precipitated crystals were collected by filtration, washed with water, and dried under reduced pressure to obtain 2-(3,5-dimethylpyrazolo)-4,6-dimethylpyrimidine (8.90 g, 88%).

Example 11

To aminoguanidine hydrochloride (5.52 g, 50 mmol), water (20 ml), acetylacetone (11 g, 110 mmol), and sodium hydrogencarbonate (4.20 g, 50 mmol) were added, and then stirred at 80° C. for 7 hours. To the reaction mixture, water (20 ml) was added, and then stirred at room temperature overnight. The precipitated crystals were collected by filtration, washed with water, and dried under reduced pressure to obtain 2-(3,5-dimethylpyrazolo)-4,6-dimethylpyrimidine (6.07 g, 60%).

Example 12

To aminoguanidine hydrochloride (5.52 g, 50 mmol), water (20 ml), acetylacetone (11 g, 110 mmol), and potassium carbonate (6.91 g, 50 mmol) were added, and then stirred at 80° C. for 7 hours. To the reaction mixture, water (20 ml) was added, and then stirred at room temperature overnight. The precipitated crystals were collected by filtration, washed with water, and dried under reduced pressure to obtain 2-(3,5-dimethylpyrazolo)-4,6-dimethylpyrimidine (5.26 g, 52%).

What is claimed is:

1. A method for producing a pyrimidinylpyrazole compound represented by general formula (1), (Formula 1)

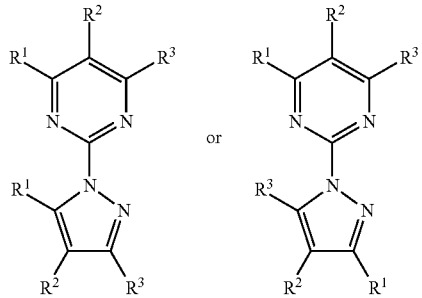

wherein aminoguanidine represented by general formula (2)

(Formula 2)

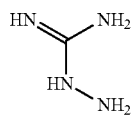

or its salt is reacted with a β-diketone compound represented by general formula (3)

(Formula 3)

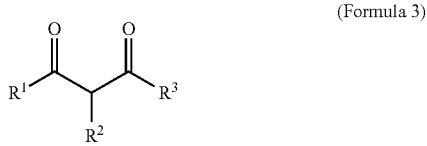

in water in the presence of a base selected from alkali metal acetates to produce the pyrimidinylpyrazole compound:

wherein $R^1$ and $R^3$ are each independently an alkyl group having 1 to 4 carbon atoms, and $R^2$ is a hydrogen atom or an alkyl group having 1 to 4 carbon atoms.

2. The method according to claim 1, wherein a 2-fold or higher molar equivalent of the β-diketone compound is used with respect to aminoguanidine.

* * * * *